United States Patent [19]

Campan et al.

[11] Patent Number: 4,761,407

[45] Date of Patent: Aug. 2, 1988

[54] SOLID GALENICAL FORM FOR ORAL ADMINISTRATION, AND THE PROCESS FOR ITS PREPARATION

[75] Inventors: Jean-Jacques Campan, Courbevoie; Roberto Lombardi, Chatou, both of France

[73] Assignee: Rhone-Poulenc Sante, Courbevoie, France

[21] Appl. No.: 789,365

[22] Filed: Oct. 22, 1985

Related U.S. Application Data

[63] Continuation of Ser. No. 436,683, Oct. 26, 1982, abandoned.

[30] Foreign Application Priority Data

Oct. 26, 1981 [FR] France .................................. 81 20048

[51] Int. Cl.$^4$ ...................... A61K 31/57; A61K 31/19; A61K 9/22

[52] U.S. Cl. .................................. 514/179; 514/557; 514/772; 514/774; 514/784; 514/785; 514/948; 514/960

[58] Field of Search ............... 514/772, 774, 784, 785, 514/948, 960, 179, 557; 424/16

[56] References Cited

U.S. PATENT DOCUMENTS

| | | | |
|---|---|---|---|
| 3,265,629 | 8/1966 | Jensen | 424/16 |
| 3,439,089 | 4/1969 | Cherkas et al. | 424/78 |
| 4,102,806 | 7/1978 | Kondo et al. | 424/38 |

Primary Examiner—J. R. Brown
Assistant Examiner—Jacqueline M. Stone
Attorney, Agent, or Firm—Stevens, Davis, Miller & Mosher

[57] ABSTRACT

New solid galenical form for oral administration, consisting of a mixture of one or more active products and two or more excipients which can be liquefied at a temperature compatible with the active product or products, and which are solid at ambient temperature.

3 Claims, No Drawings

SOLID GALENICAL FORM FOR ORAL ADMINISTRATION, AND THE PROCESS FOR ITS PREPARATION

This application is a continuation of application Ser. No. 436,683, filed 10/26/82.

The present invention relates to a new solid galenical form for oral administration and to the process for its preparation.

The known solid pharmaceutical forms for oral administration, containing a unit dose of one or more active principles, are mainly tablets, coated tablets or the like, and gelatine capsules. Although industry has mastered the preparation of such formulations, it is nevertheless true that the processes used, in particular for the manufacture of tablets, are long and complicated and they involve virtually unavoidable losses. For example, the process for the manufacture of tablets is essentially a batch process which must proceed via, in general, 5 to 10 intermediate stages, each of which has to be rigorously controlled. Thus, the overall process can last 1 to 2 weeks. At each intermediate stage, there are unavoidable losses which it is very difficult to reduce. It must also be noted that the multiplicity of manufacturing stages results in a multiplicity of production installations, the effect of which is to make it more difficult to observe good manufacturing practices (emission of dust, contact between the operator and the product, and the like).

Furthermore, tablets are manufactured essentially by mixing powders of different bulk density and different particle size, which makes it more difficult to obtain really uniform doses of the active principle in each tablet and hence to obtain perfectly homogeneous batches of tablets, which constitutes a major disadvantage in the case of active principles used at very low doses.

A new solid galenical form, hereafter referred to as an "instantaneous solidified oral form" or "ISOF", has now been found which has the advantage, over the forms known hitherto, that it can be prepared more rapidly by a continuous process and that it leads to batches of unit doses in which the active principle is distributed very uniformly, even in the case of low doses; it is this new solid galenical form which constitutes one of the subjects of the present invention.

According to the invention, the "ISOF" consists of one or more active principles dissolved or dispersed in two or more excipients which can be liquefied at a temperature above ambient temperature, e.g. 35° C., but below a temperature at which the active principle or principles would be adversely affected, which are compatible with the active principle or principles and are solid at ambient temperature, and which can release the active principle or principles in water or a physiological liquid. It is to be understood that the expression "galenical form" as used in this specification and the accompanying claims denotes pharmaceutical or veterinary compositions generally and is not limited to compositions containing one or several organic ingredients as contrasted with pure chemical substances.

In the galenical form according to the invention, the active principle is dispersed in the form of particles which are generally much finer than in the customary solid oral galenical forms or, preferably, dissolved. This principally results in a change in the bioavailability of the active principle, which is expressed in the release and/or absorption of the active principle and consequently in the metabolism.

The "ISOFs" according to the invention must correspond to precise physical characteristics, which depend mainly on the active principle and its dosage. The essential general characteristics of the "ISOFs" relate to their appearance, their form, their hardness, their weight, their disaggregation and dispersion times and the storage temperature.

The appearance of the "ISOFs" must be homogeneous on the surface and within the compositions, and their surface must be level and smooth.

The forms of the "ISOFs" can vary extremely widely, but their geometry must be compatible with easy mould release and with the method of administration.

The consistency of the "ISOFs" can vary. In general, it must be such that the "ISOF" withstands handling by the user or withstands impacts, e.g. being dropped 1 meter from the ground. Furthermore, their cohesion must be such that they can be removed from their container without harm to their physical integrity.

The weight of the "ISOFs" can be between a few tens of milligrams and several hundred milligrams, the lower limit depending on the precision of the measurement of the amount of "ISOF" in the container, and the upper limit being related to the maximum size of the "ISOF" which can be taken by the patient.

The disaggregation and dispersion time of the "ISOF" is preferably less than 45 minutes in water or an artificial physiological liquid at 37±2° C., with periodic stirring.

The "ISOF" must remain in the solid form during storage, i.e. generally at a temperature below 30° C. However, the m.p. of the composition, which depends on the stability of the active principle, can be considerably higher.

According to the invention, there is a general process for the preparation of "ISOFs", but it must be adapted to suit each particular case, taking into account the specific properties of the active principles used.

A generally preferred process for the preparation of "ISOFs" can be summarised as follows:

1—starting from primary excipients, i.e. substances normally used in galenical pharmacy and listed in the pharmacopoeias, chosen according to their ability to solubilise or disperse the active principles in question, a secondary excipient ($SE_1°$) is prepared which is capable of forming a phase of lipophilic, hydrophilic or amphoteric character, depending on the nature and the properties of the active principles, 2—the active principle is solubilised or dispersed in the secondary excipient $SE_1°$, if appropriate in the presence of a primary excipient assisting its solubilisation or dispersion, to give a phase $\phi1$, which is kept liquid at a sufficiently high temperature, 3—starting from primary excipients, a secondary excipient ($SE_2°$) is prepared which is of hydrophilic, lipophilic or amphoteric character, depending on the nature of the secondary excipient $SE_1°$, and which forms a phase $\phi2$, which is kept liquid at a sufficiently high temperature, it being understood that if $SE_1°$ is lipophilic, $SE_2°$ is hydrophilic or amphoteric, if $SE_1°$ is hydrophilic, $SE_2°$ is lipophilic or amphoteric, and if $SE_1°$ is amphoteric, $SE_2°$ is lipophilic, hydrophilic or amphoteric, 4—the phase $\phi1$ (or $\phi2$) is then dispersed in the phase $\phi2$ (or $\phi1$) at the same temperature, to give a mixture $\phi3$ of homogeneous consistency, which is liquid at a temperature above the ambient storage temperature, 5—after the phase $\phi 3$ has cooled to a temperature near the solidification temperature, it is poured into suitable containers to give unit "ISOFs", which solidify on cooling, acquiring the cohesion necessary for their subsequent handling, and 6—the container in which the "ISOFs" are present is closed by any suitable means, e.g. by heat-sealing or extrusion.

In general, the whole of the process is carried out without taking any particular precautions as regards the ambient temperature and the relative humidity.

Non-ionic and/or amphoteric surface-active agents, terpenes, aminoacids, polypeptides, alcohols and fatty acids, optionally esterified, polyols, and mixtures thereof are generally used to manufacture the "ISOFs".

Amongst the primary excipients which are particularly suitable, there may be mentioned cetyl alcohol, linoleic acid, isopropyl myristate, glycerol monostearate, gelatine, lecithin, leucine, lysine, glycerophosphoric acid, propylene glycol, glycerol, water, alcohol, and terpenes, such as cineol, menthol, eucalyptol or camphor, this list not implying a limitation.

It is important to point out that the excipients suitable for manufacturing the "ISOFs" cannot be used to manufacture suppositories or "LYOCS". Conversely, the excipients used for these forms of administration, such as triglycerides, polyethylene glycols or lactose, are not suitable for manufacturing the "ISOFs".

It is particularly advantageous to choose the proportions of the various excipients so as to obtain eutectic mixtures, i.e. mixtures of excipients capable of giving molten or liquefied systems at temperatures below the m.p. of each of the constituents, for the purpose of avoiding possible degradation of the active principle or principles.

To carry out the process according to the invention, it can be advantageous to prepare reference secondary excipients which can be modified according to the specific properties of the active principles to be formulated. Taking account of the known characteristics of an active product, it will be possible to choose the type of secondary excipient which permits the most appropriate formulation.

The essential physico-chemical properties which are taken into consideration when choosing the secondary excipient are the solubility, the m.p., the lipophilic, hydrophilic or amphoteric character and the stability as a function of the temperature, but other properties, such as the crystalline form, may be involved. The secondary excipient $SE_1°$ will therefore be chosen so that the dissolution or dispersion of the active principle is carried out at as low a temperature as possible. The active principle dissolved or dispersion in the secondary excipient $SE_1°$ forms the phase $\phi 1$. In the large majority of cases, the phase $\phi 1$ thus obtained cannot be poured directly to form the "ISOF" because either its solubility in water or artificial physiological liquids is virtually zero or too low, after solidification, or it forms a liquid phase which cannot be solidified at ambient temperature. It is therefore necessary to complement the phase $\phi 1$ with a phase $\phi 2$, consisting of a secondary excipient $SE_2°$ which constitutes a carrier capable of keeping the phase $\phi 1$ in the liquid state at a temperature generally above 35° C., and of leading to solidification at ambient temperature so as to form the "ISOF", which will be soluble or dispersible in water or natural or artificial physiological liquids.

Furthermore, it may be necessary to add, to the phase $\phi 1$ or $\phi 2$, primary excipients capable of fixing the volatile constituents, such as certain terpenes.

According to the present invention, the final form in which the medicament is presented is preferably obtained by laying a flexible and tearable foil, in a known manner, over the containers in which the unit "ISOFs" are present. The flexible and tearable foil must be compatible with the "ISOF". It can consist of a thin foil of aluminium or one of its alloys. Preferably, the new pharmaceutical form is packaged in blister packs.

The "ISOFs" according to the present invention are particularly useful for the preparation of unit doses containing a low dose of active product (corticoids, antihistamines, liposoluble vitamins, and the like) or a sensitive product, such as an aminoacid (methionine, cysteine, cystine), a protein or an enzyme (pancreatin, trypsin and the like).

By appropriate choice of the excipients, the "ISOFs" according to the present invention can be used for the formulation of active principles whose release in the organism must be controlled and gradual over a period of time.

The examples which follow, which are given without implying a limitation, show how the invention can be put into practice. The proportions of the various constituents are expressed by weight.

A—Preparation of blank "ISOFs", i.e. "ISOFs" without active product

EXAMPLE 1

Preparation of a blank "ISOF" of lipophilic character

A mixture of water (3 parts), ethanol (6 parts), propylene glycol (5 parts) and lecithin (5 parts) is prepared at a temperature of the order of 20° C., with slow stirring, to give a phase $\phi 2$.

Linoleic acid (5 parts) and isopropyl myristate (2 parts) are added to cetyl alcohol (70 parts) molten at 50° C. A solution obtained by successively dissolving menthol (0.25 part), eucalyptol (0.5 part) and camphor (0.25 part) in cineol (3 parts), at a temperature of the order of 20° C., is added to the resulting solution. This gives a phase $\phi 1$.

The phase $\phi 1$ is added to the phase $\phi 2$, with slow stirring, at a temperature of between 45° and 50° C.

This gives a homogeneous solution of an excipient having a lipophilic character.

EXAMPLE 2

Preparation of a blank "ISOF" of lipophilic character

A phase $\phi 2$ is obtained by melting glycerol monostearate (80 parts).

A mixture consisting of lecithin (1 part), glycerophosphoric acid (1 part) and propylene glycol (1 part) is prepared at a temperature of between 45° and 50° C. A solution obtained by dissolving cineol (5 parts) and eucalyptol (5 parts) in 95° strength alcohol (7 parts), is added to the resulting solution at a temperature of between 50° and 55° C. This gives a phase $\phi 1$, which is added to the phase $\phi 2$, with slow stirring, at a temperature of between 50° and 55° C. This gives a homogeneous solution of an excipient having a lipophilic character.

EXAMPLE 3

Preparation of a blank "ISOF" of lipophilic character

A mixture of 95° strength alcohol (1 part), cineol (1 part), menthol (1 part), eucalyptol (1 part) and camphor (1 part) is prepared, with slow stirring, at a temperature of 20° C., and lecithin (7 parts), heated to a temperature of between 35° and 40° C., is added thereto to give a phase $\phi 1$.

A mixture of isopropyl myristate (85 parts), cetyl alcohol (1 part), linoleic acid (1 part) and glycerol monostearate (1 part) is prepared, with slow stirring, at the same temperature, to give a phase $\phi 2$.

The phase $\phi 1$ is added to the phase $\phi 2$, with stirring, at the same temperature (40° C.). This gives a homogeneous solution of an excipient having a lipophilic character.

EXAMPLE 4

Preparation of a blank "ISOF" of hydrophilic character

A mixture of water (60 parts), gelatine (5 parts), lecithin (1 part) and propylene glycol (5 parts) is prepared, with slow stirring, at a temperature of 50° C., to give a phase $\phi 1$.

A mixture of 95° strength alcohol (10 parts), cineol (3 parts), menthol (0.5 part), eucalyptol (5 parts), camphor (0.5 part) and isopropyl myristate (1 part) is prepared, with slow stirring, at the same temperature, to give a phase $\phi 2$.

The phase $\phi 2$ is added to the phase $\phi 1$, with stirring, at the same temperature (50° C.). This gives a homogeneous solution of an excipient having a hydrophilic character.

EXAMPLE 5

Preparation of a blank "ISOF" of hydrophilic character

A mixture of water (75.5 parts), gelatine (5 parts), lecithin (2 parts), lysine (0.5 part), leucine (0.5 part) and propylene glycol (5 parts) is prepared, with slow stirring, at a temperature of 50° C., to give a phase $\phi 1$.

A mixture of 95° strength alcohol (5 parts), cineol (5 parts), menthol (0.5 part), eucalyptol (0.5 part) and camphor (0.5 part) is prepared, with slow stirring, at the same temperature (50° C.), to give a phase $\phi 2$.

The phase $\phi 2$ is added to the phase $\phi 1$, with stirring, at the same temperature. This gives a homogeneous solution having a hydrophilic character.

EXAMPLE 6

Preparation of a blank "ISOF" of amphoteric character

Glycerol monostearate (1 part) is melted at a temperature of between 55° and 60° C. and a mixture of cetyl alcohol (20 parts) and isopropyl myristate (1 part) is added, with slow stirring, at 55°-60° C., to give a phase $\phi 2$.

A mixture of water (20 parts), gelatine (1 part), lecithin (5 parts), lysine (1 part), leucine (1 part), propanetriol (10.5 parts) and propylene glycol (10.5 parts) is prepared, with slow stirring, at a temperature of 45° to 50° C., and a mixture of 95° strength alcohol (25 parts), cineol (3 parts), menthol (0.25 part), eucalyptol (0.5 part) and camphor (0.25 part), at the same temperature, is added thereto to give a phase $\phi 1$.

The phases $\phi 1$ and $\phi 2$ are heated to a temperature of between 40° and 50° C. and the phase $\phi 1$ is then added to the phase $\phi 2$ at the same temperature, with stirring.

This gives a homogeneous solution having an amphoteric character.

B—Preparation of "ISOFs" containing an active product

EXAMPLE 7

"ISOFs" containing 150 mg of ketoprofen for a total weight of 1,000 mg are prepared.

A mixture of 95° strength alcohol (2 parts), propylene glycol (10 parts), menthol (0.5 part) and eucalyptol (15 parts) is prepared, with slow stirring, at a temperature of between 60° and 65° C., and ketoprofen (15 parts) and glycerol monostearate (0.1 part) are added thereto. This gives a phase $\phi 1$.

A mixture of water (37.4 parts), gelatine (18 parts) and lecithin (2 parts) is prepared at the same temperature. This gives a phase $\phi 2$. The phase $\phi 1$ is added to the phase $\phi 2$, at the same temperature, so as to give a homogeneous mixture.

This mixture is poured onto a cellular sheet so that each cell contains 1,000 mg of the mixture. After cooling, whitish rigid "ISOFs" are obtained which have a slight terpene taste and the characteristic smell of the volatile terpenes used.

A unit "ISOF" obtained in this way has a disaggregation and dispersion time of less than 20 minutes in water at $37\pm2°$ C.

EXAMPLE 8

"ISOFs" containing 100 mg of ketoprofen for a total weight of 1,000 mg are prepared.

A mixture of 95° strength alcohol (2 parts) and propylene glycol (10 parts) is prepared, with slow stirring, at about 20° C.; it is heated to a temperature of between 60° and 65° C. and a mixture of eucalyptol (15 parts), menthol (0.5 part) and propanetriol (5 parts) is added thereto. A mixture of ketoprofen (10 parts) and glycerol monostearate (0.2 part) is added to the mixture thus obtained, at a temperature of between 60° and 65° C. This gives a phase $\phi 1$.

A mixture of water (37.3 parts), gelatine (18 parts) and lecithin (2 parts) is prepared at a temperature of between 60° and 65° C. This gives a phase $\phi 2$.

The phase $\phi 1$ is added to the phase $\phi 2$, at a temperature of between 60° and 65° C., so as to give a homogeneous mixture.

This mixture is poured onto a cellular sheet so that each cell contains 1,000 mg of the mixture. After cooling, whitish "ISOFs" of soft consistency are obtained which have a slight terpene taste and the characteristic smell of the volatile terpenes used.

A unit "ISOF" obtained in this way has a disaggregation and dispersion time of less than 5 minutes in water at a temperature of $37\pm2°$ C.

EXAMPLE 9

"ISOFs" containing 150 mg of ketoprofen for a total weight of 1,000 mg are prepared.

A mixture of eucalyptol (20 parts), menthol (0.5 part), camphor (0.5 part) and alcohol (2 parts) is prepared, with slow stirring, at a temperature of about 20° C., to give a secondary excipient $SE_1°$; this is heated to a temperature of between 50° and 55° C. and ketoprofen (15 parts) is added thereto. This gives a homogeneous liquid phase $\phi 1$.

A mixture of water (36 parts), gelatine (10 parts), lecithin (5 parts), glycerol monostearate (0.5 part), propanetriol (5 parts) and propylene glycol (5 parts) is prepared at a temperature of between 40° and 50° C. This gives a homogeneous phase $\phi 2$, which is added to the phase $\phi 1$ at the same temperature of 50° C.

This mixture is poured onto a cellular sheet so that each cell contains 1,000 mg of the mixture. After cooling, whitish "ISOFs" of intermediate consistency are obtained which have a slight terpene taste and the characteristic smell of the volatile terpenes used.

A unit "ISOF" obtained in this way has a disaggregation and dispersion time of less than 10 minutes in water at a temperature of 37±2° C.

EXAMPLE 10

"ISOFs" containing 2.5 mg of prednisone for a total weight of 100 mg are prepared.

A mixture of eucalyptol (10 parts), propanetriol (10 parts) and "Tween 80" (1 part) is prepared, with slow stirring, at a temperature of 30° C., and prednisone (2.5 parts) is added thereto to give a phase $\phi 1$, which is heated to 45° C.

A mixture of water (63.5 parts), gelatine (2 parts) and propanetriol (10 parts) is prepared at the same temperature. This gives a homogeneous phase $\phi 2$, which is added to the phase $\phi 1$, at the same temperature of 45° C., to give a homogeneous liquid mixture.

This mixture is poured onto a cellular sheet so that each cell contains 100 mg of the mixture. After cooling, whitish "ISOFs" of soft consistency are obtained which have a slight terpene taste and the characteristic smell of the volatile terpenes used.

A unit "ISOF" has a disaggregation and dispersion time of less than 10 minutes in water at 37±2° C.

EXAMPLE 11

By following the procedure of Example 10, but replacing the prednisone by prednisolone, "ISOFs" are obtained which contain 2.5 mg of prednisolone for a total weight of 100 mg.

We claim:

1. A solid pharmaceutical or veterinary composition for oral administration, which comprises an active ingredient selected from the group consisting of ketoprofen, prednisone and prednisolone dissolved or dispersed in a pharmaceutically or veterinarily acceptable excipient mixture which liquefies at a temperature above ambient temperature, which excipient mixture is compatible with the active ingredient and is solid at ambient temperature, and which releases the active ingredient in water or after oral administration, when prepared by the process which comprises:
   (a) dissolving or dispersing the active ingredient in a first lipophilic, hydrophilic or amphoteric excipient phase, the said first excipient phase being kept liquid at a temperature above ambient temperature, and
   (b) mixing the liquid phase thus obtained with a second lipophilic, hydrophilic or amphoteric liquid excipient phase;
   the first excipient phase and the second excipient phase each comprising an excipient or excipients selected from the group consisting of: as lipophilic excipients, cetyl alcohol, linoleic acid, isopropyl myristate, cineol, menthol, eucalyptol and camphor; as hydrophilic excipients, water, ethanol, propylene glycol, glycerol, gelatine, leucine and lysine: and, as amphoteric excipients, lecithin, glycerol monostearate and glycerophosphoric acid;
   the second excipient phase being hydrophilic or amphoteric when the first excipient phase is lipophilic, the second excipient phase being lipophilic or amphoteric when the first excipient phase is hydrophilic, and the second excipient phase being lipophilic, hydrophilic or amphoteric, when the first excipient phase is amphoteric,
   the solution obtained being liquid and homogeneous at a temperature above ambient temperature, and cooling to solidify the said solution to a homogeneous solid composition in unit dosage form.

2. A solid pharmaceutical or veterinary composition according to claim 1 in which the excipients are liquid at a temperature above 35° C.

3. A solid pharmaceutical or veterinary composition according to claim 1, in which a eutectic mixture of excipients is used.

* * * * *